US006936426B2

(12) United States Patent
Smith et al.

(10) Patent No.: US 6,936,426 B2
(45) Date of Patent: Aug. 30, 2005

(54) DETECTION OF ANTIBODY MEDIATED INFLAMMATORY AUTO-IMMUNE DISORDERS

(75) Inventors: Terry J. Smith, Manhattan Beach, CA (US); William W. Cruikshank, Westford, MA (US)

(73) Assignee: Harbor-UCLA Research and Education Institute, Torrance, CA (US)

( * ) Notice: Subject to any disclaimer, the term of this patent is extended or adjusted under 35 U.S.C. 154(b) by 306 days.

(21) Appl. No.: 10/046,651

(22) Filed: Oct. 19, 2001

(65) Prior Publication Data

US 2003/0022911 A1 Jan. 30, 2003

Related U.S. Application Data

(63) Continuation of application No. 09/684,601, filed on Oct. 6, 2000, now abandoned.

(51) Int. Cl.[7] .............................................. G01N 33/53
(52) U.S. Cl. .......................... 435/7.1; 435/29; 435/7.92
(58) Field of Search ........................... 435/7.1, 29, 7.92

(56) References Cited

PUBLICATIONS

Ishibashi et al., IUBMB Life, vol. 51:25–31, 2001.*
Rotella et al. J. Clin. Endocrinol. Metabol. 1986 62:357–367.
Sciaky et al. J. Immunol. 2000 164:3806–3814.
Smith et al. Am. J. Pathol. 1997 151:317–322.
Lim et al. J. Immunol. 1996 156:2566–2570.

* cited by examiner

Primary Examiner—Patrick J. Nolan
(74) Attorney, Agent, or Firm—McDermott Will & Emery LLP

(57) ABSTRACT

The present invention describes a method to detect connective tissue pathologies associated with Graves' disease ophthalmopathy and other antibody mediated inflammatory autoimmune diseases. The detection method comprises obtaining a sample from a patient suffering from an antibody-mediated inflammatory autoimmune disorder and measuring Interleukin 16 (IL-16) or RANTES produced by thyroid associated ophthalmopathy fibroblasts to indicate the presence or severity.

4 Claims, 6 Drawing Sheets

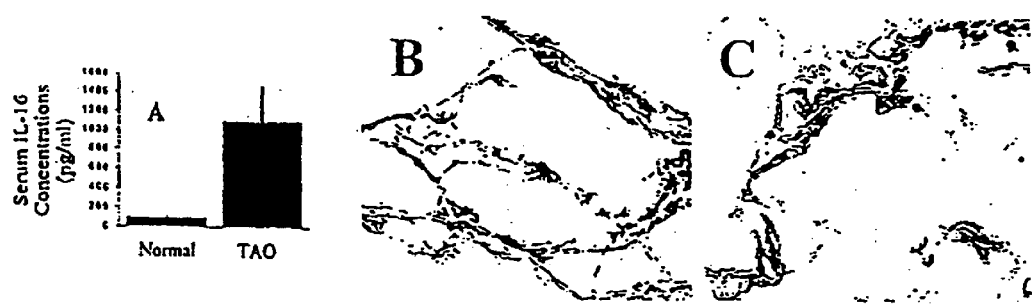
Fig. 3(A) in grant Serum concentrations of IL-16 are dramatically elevated in patients with active TAO; (B) IL-16 and (C) PGHS-2 protein can be detected in orbital tissue in TAO.
FIGURE 3 A, B & C

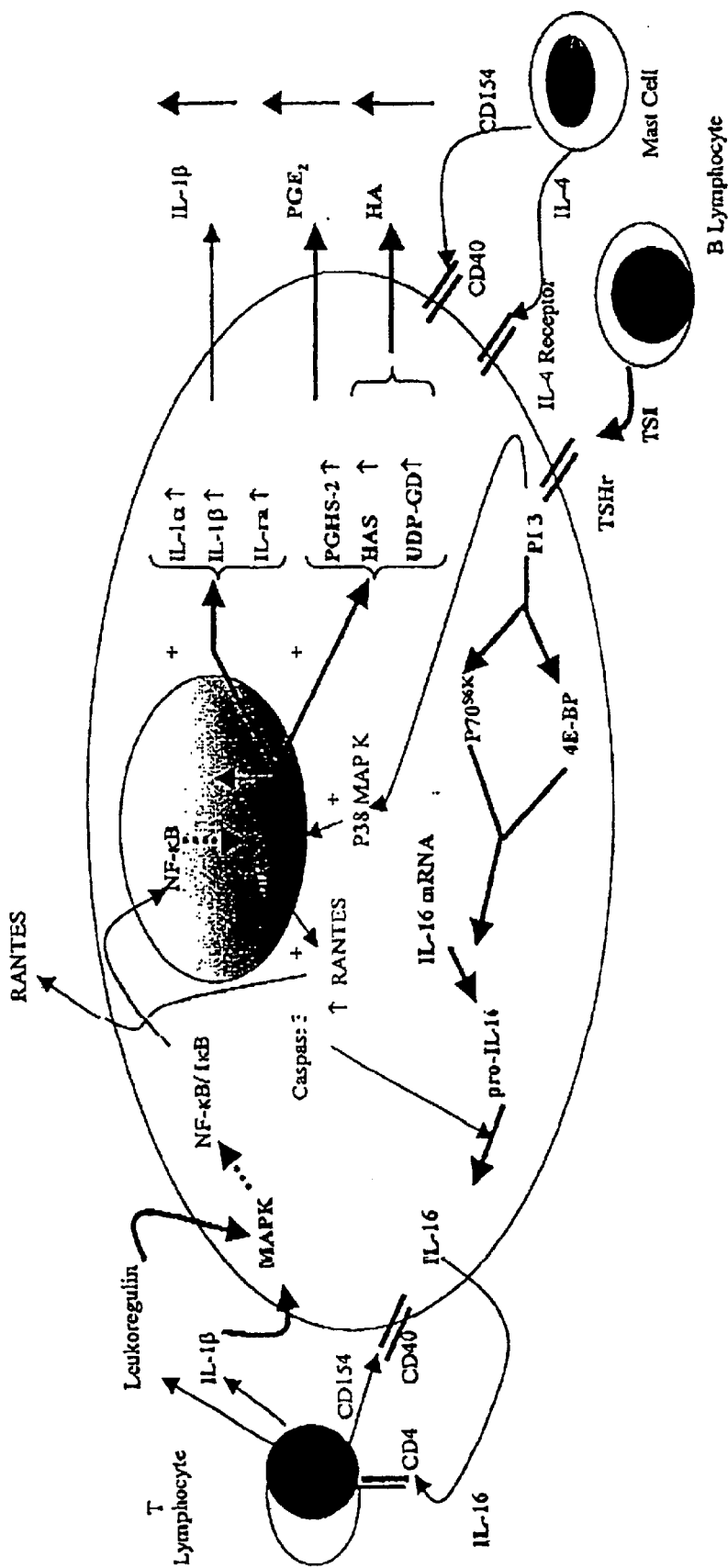
FIGURE 5 (overview)

DETECTION OF ANTIBODY MEDIATED INFLAMMATORY AUTO-IMMUNE DISORDERS

RELATED INFORMATION

This application is a continuation of U.S. Ser. No. 09/684,601, filed on Oct. 6, 2000 now abandoned. The priority of this prior application is expressly claimed and the disclosure of this prior application is hereby incorporated by reference in its entirety.

FIELD OF INVENTION

The present invention describes a novel therapy to alleviate antibody-mediated inflammatory auto-immune diseases and other pathologies having a common underlying mechanism. One example is the connective tissue pathologies associated with Graves' disease also known as Thyroid-Associated Ophthalmopathy (TAO). The therapeutic component of this invention comprises administering to a patient suffering from an antibody-mediated inflammatory auto-immune disorder a compound that blocks the expression or induction of Interleukin 16 (IL-16) and/or RANTES by antibodies specific to Graves' disease to decrease the proliferation of CD4-bearing lymphocytes at the site of the disease. Especially preferred blockers of IL-16 induction for use in the therapeutic methods of the present invention are rapamycin and PD098059, and an especially preferred blocker of RANTES induction for use in the present invention is compound SB203580. The present invention also includes diagnostic tests and methods to determine the presence of antibody-activated fibroblasts in a patient by assaying the levels of IL-16 and/or RANTES in a biological sample obtained from the patient.

BACKGROUND

Graves' disease is caused by a hyper-functioning, diffuse, hyperplastic thyroid goiter, often accompanied by infiltrative ophthalmopathy and infiltrative dermopathy. Graves' disease is present in 1.5% to 2% of women in the United States, but is only one-tenth as common among men. Familial predisposition has been noted frequently. There is also a well-defined relationship between Graves' disease and other auto-immune diseases, such as pernicious anemia and rheumatoid arthritis, which occur with greater than normal frequency in patients with Graves' disease. With Thyroid-Associated Ophthalmopathy (TAO), there is characteristic tissue remodeling in the orbital area, including lymphocyte infiltration, hyaluronan accumulation and inflammation.

TAO remains a difficult clinical problem because currently available treatments are either ineffective or have significant side effects, due largely to the lack of specificity of the treatment. The absence of any satisfactory therapies is also directly attributable to the current poor understanding of the fundamental disease process. The orbital space is constrained by bone and thus small increases in the volume of soft tissue will cause the anterior displacement of the eye (proptosis). Proptosis occurs in TAO, where the endomysial connective tissue and fat/connective tissue in the orbit are infiltrated with immunocompetent cells such as lymphocytes, macrophages and mast cells. (Smith, T. J., Bahn, R. S. and Gorman, C. A.: Connective tissue, glycosaminoglycans and diseases of the thyroid. Endocrine Rev. 10:366–391, 1989). The inflammatory reaction is sometimes intense. A major component of the tissue remodeling seen in the orbit in TAO relates to the accumulation of the non-sulfated glycosaminoglycan, hyaluronan. Hyaluronan possesses a set of rheological properties that render the molecule extraordinarily hydrophilic (Smith, T. J., Bahn, R. S. and Gorman, C. A.: Connective tissue, glycosaminoglycans and diseases of the thyroid. Endocrine Rev. 10:366–391, 1989). Thus, even a small increase in the hyaluronan content of a tissue could increase its volume dramatically. In the setting of the bony orbit, such an increase could yield catastrophic consequences to the integrity of soft tissue structures, innervation and vascularity.

Debate exists as to whether the primary focus of the pathogenic process is directed at the extraocular musculature or the connective/adipose tissue in the orbit. In many cases, enlargement of the extraocular musculature appears to be more dramatic than that of the fat pad (Smith, T. J., Bahn, R. S. and Gorman, C. A.: Connective tissue, glycosaminoglycans and diseases of the thyroid. Endocrine Rev. 10:366–391, 1989). The work of Smelser provided strong evidence that TAO is a fibroblast-related disease process (Smelser, G. K.: A comparative study of experimental and clinical exophthalmos. Am. J. Ophthalmol. 20:1189–1203, 1937). This group described the early disease as similar edematous changes occurring in both muscle and fat interstitium with minimal muscle degeneration. Subsequent light and transmission electron microscopic studies have confirmed the preservation of the motor elements of the muscles until very late in the disease process. The endomysium, rich with fibroblasts, accumulates hyaluronan, accounting for the volume changes observed in muscle.

Physicians and medical researchers have a growing awareness of the complexity with which connective tissue is regulated and of the diverse influences that elements of this tissue exert on neighboring cell types. Fibroblasts vary with regard to anatomic region of origin and synthesize numerous small regulatory molecules including cytokines and growth factors (Fries, K. M., Blieden, T., Looney, R. J., Sempowski, G. D., Slvera, M. R., Willis, R. A. and Phipps, R. P.: Evidence of fibroblast heterogeneity and the role of fibroblast populations in fibrosis. Clin. Immunol. Immunopath. 72:283–292, 1994). Research has demonstrated that orbital fibroblasts are vastly different from those found in other anatomic locations in regard to their biosynthetic repertoires, their responses to hormones and growth factors and the extracellular matrix that they lay down (Smith, T. J., Aftab, A., Hogg, M. G. and Higgins, P. J.: Interferon-γ is an inducer of plasminogen activator inhibitor type 1 in human orbital fibroblasts. Am. J. Physiol. 263:C24–C29, 1992; Smith, T. J., Bahn, R. S., Gorman, C. A. and Cheavens, M.: Stimulation of glycosaminoglycan accumulation by interferon gamma in cultured human retroocular fibroblasts. J. Clin. Endocrinol. Metab. 72:1169–1171, 1991; Smith, T. J.: Dexamethasone regulation of glycosaminoglycan synthesis in cultured human skin fibroblasts: similar effects of glucocorticoid and thyroid hormones. J. Clin. Invest. 74:2157–2163, 1984; Smith, T. J., Bahn, R. S. and Gorman, C. A.: Hormonal regulation of hyaluronate synthesis in cultured human fibroblasts: evidence for differences between retroocular and dermal fibroblasts. J. Clin. Endocrinol. Metab. 69:1019–1023, 1989). Controversy also exists with regard to the phenotypes of lymphocytes predominating in the orbit of patients with TAO (McLachlan, S. M., Prummel, M. F. and Rapoport, B.: Cell-mediated or humoral immunity in Graves' ophthalmopathy? Profiles of T-cell cytokines amplified by polymerase chain reaction from orbital tissue. J. Clin. Endocrinol. Metab. 78:1070–1074, 1994; Jaume, J. C., Portolano, S., Prummel, M. F., McLachlan, S. M. and Rapoport, B., Molecular cloning and characterization of genes for antibodies generated by orbital tissue-infiltrating B-cells in Graves' ophthalmopathy. *J. Clin. Endocrinol. Metab.* 78:348–352, 1994; De Carli, M., D'Elios, M. M., Mariotti, S., Marcocci, C., Pinchera, A., Ricci, M., Romagnani, S. and Del Prete, G.: Cytolytic T cells with Th1-like cytokine profile predominate in retroorbital lymphocyte infiltrates of Graves' ophthalmopathy. *J. Clin. Endocrinol. Metab.* 77:1120–1124, 1993; Grubeck-Loebenstein, B., Trieb, K., Sztankay, A, Holter, W., Anderi, H. and Wick, G.: Retrobulbar T cells from patients with Graves' ophthalmopathy are CD8$^+$ and specifically recognize autologous fibroblasts. *J. Clin. Invest.* 93:2738–2743, 1994).

The selective targeting of orbital connective tissue for activation in Graves' disease is not currently understood. A central question is why activated T and B lymphocytes are trafficked to the orbit. Interest has centered on the successful cloning of the Thyroid Stimulating Hormone Receptor (TSH-R). TSH-R is implicated in the glandular component of Graves' disease by virtue of its activation by Thyroid Stimulating Immunoglobulin (TSI) resulting in hyperthyroidism. Recently, preliminary evidence was introduced suggesting that TSIs are heterogeneous (Drexhage, H. A.: Autoimmunity and thyroid growth. Where do we stand? *Eur. J. Endocrinol.* 135:39–45, 1996). Moreover, these different sub-classes of TSI might activate distinct signaling pathways in the thyroid. Until now, little insight existed concerning the actions of TSI on orbital fibroblasts. Thus, no connection had been identified between the presence of these immunoglobulins and the pathogenesis of TAO. A number of investigators have speculated that the TSH-R might represent an auto-antigen relevant to TAO if anatomically restricted expression, shared by the orbit and the thyroid, could be established. Indeed, mRNA encoding the TSH-R has been extracted from the orbits of patients with severe TAO as well as from normal orbital tissue (Feliciello, A., Porcellini, A., Ciullo, I., Bonavolonta, G., Avvedimento, E. V. and Fenzi, G., Expression of thyrotropin-receptor mRNA in healthy and Graves' disease retro-orbital tissue. Lancet 342:337–338, 1993). Moreover, TSH-R mRNA has been detected in orbital fibroblasts by PCR amplification (Heufelder, A. E., Dutton, C. M., Sarkar, G., Donovan, K. A. and Bahn, R. S.: Detection of TSH receptor RNA in cultured fibroblasts from patients with Graves' ophthalmopathy and pretibial dermopathy. *Thyroid* 3:297–300, 1993).

Pro-inflammatory cytokines also have been implicated in the pathogenesis of TAO. A recent report suggested the presence of immunoreactive IL-1α in orbital connective tissue from patients with severe TAO (Heufelder, A. E. and Bahn, R. S.: Detection and localization of cytokine immunoreactivity in retro-ocular connective tissue in Graves' ophthalmopathy. *European J. Invest.* 23:10–17, 1993. 22. Dinarello, C. A.: Biologic basis for interieukin-1 in disease. *Blood* 87:2095–2147, 1996). IL-1 is a family of two cytokines designated IL-1α and IL-1β, each encoded by a separate gene but with substantial overlap in their biological actions (Dinarello, C. A.: Biologic basis for interieukin-1 in disease. *Blood* 87:2095–2147, 1996). IL-1α is primarily an intracellular molecule while IL-1β is exported to the outside of the cell expressing it. It would appear that these IL-1 proteins share common receptors. Bahn has also implicated leukoregulin, a T lymphocyte-derived cytokine, in the pathogenesis of TAO (Bahn, R. S.: Cytokines in thyroid eye disease. *Thyroid* 8:415–418, 1998). Leukoregulin is a 50 kDa cytokine that is expressed by activated T lymphocytes (Mauviel, A., Redini, F., Hartmann, D. J., Pujol, J. -P. and Evans, C. H.: Modulation of human dermal fibroblast extracellular matrix metabolism by the lymphokine leukoregulin. *J. Cell Biol.* 113:1455–1462, 1991) and acts through NF-KB to up-regulate inflammatory and extracellular matrix-encoding genes.

IL-16 is a CD4-specific chemoattractant molecule not assigned to any chemokine family because the requisite cysteine signature residues for such designation are absent (Center, D. M., Kornfeld, H. and Cruikshank, W. W.: Interleukin 16 and its function as a CD4 ligand. *Immunol. Today* 17:476–481, 1996). IL-16 was originally found to be expressed by activated CD8+ lymphocytes but subsequently has been found to be produced by mast cells, bronchial epithelium and CD4+ lymphocytes. It has been cloned and found to be regulated by several factors in a cell-type-specific pattern. IL-16 is a CD4 ligand and when bound, leads to lymphocyte activation and IL-2 receptor up-regulation. It has been implicated in the pathogenesis of asthma and human auto-immune diseases such as rheumatoid arthritis and lupus. IL-16 was detected in synovial fluid and soft tissues of diseased joints (Franz, J. K., Kolb, S. A., Hummel, K. M., Lahrtz, F., Neidhart, M., Aicher, W. K., Pap, T., Gay, R. E., Fontana, A. and Gay, S.: Interleukin-16, produced by synovial fibroblasts, mediates chemoattraction of CD4$^+$ T lymphocytes in rheumatoid arthritis. *Eur. J. Immunol.* 28:2661–1998).

In addition to TAO, several other connective tissue disorders have been shown to have an antibody-mediated auto-immune component. For example, vitiligo, a depigmenting order of the skin, is caused by the destruction of melanocytes. Although the cause is still unknown, prominent theories explaining the mechanism of melanocyte destruction are autoimmune, autocytotoxicm and neural hypotheses. (S. O. Kovacs, *Vitiligo,* 38 J. Am. Acad. Dermatol. 647 (1998)). Pemphigus vulgaris is another antibody-mediated autoimmune disease affecting the skin. Antibodies against desmosomal adhesion molecules (Dsg3) are thought to be a major factor in the pathogenesis of the disease. Autoreactive T-cells, which recognize epitopes of Dsg3 in PV patients, preferentially produce TH2 cytokines such as IL-4 and IL-10. (M. Hertl and R. Riechers, *Analysis of the T cells that are Potentially Involved in Autoantibody Production in Pemphigus Vulgaris,* 26 J. Dermatol. 748 (1999)).

Polyglandular autoimmune syndrome is used to describe the dysfunction of two or more endocrine glands occurring in association with circulating antibodies directed against the affected glands. The autoimmune nature of the syndrome is caused by the presence of lymphocytic infiltration of the affected gland, organ-specific autoantibodies, cellular immune defects, and an association with the immune response genes. The principal endocrine components include adrenal insufficiency, autoimmune thyroid disease, insulin-dependent diabetes mellitus, and premature gonadal failure. (M. Leshin, Polyglandular Autoimmune Syndromes, 290 Am. J. Med. Sci. 77 (1985); W. J. Riley, Autoimmune Polyglandular Syndromes, 38 Horm. Res. 9 (Suppl. 2) (1992)).

Type 1 diabetes, a disease affecting several million every year, is caused by autoimmune destruction of the B-cells in the pancreatic islets of Langerhans which produce insulin. Although it is required to be present, a certain genetic phenotype does not appear sufficient on its own to trigger the disease. Many believe that infectious agents are important environmental factors which help trigger T-cell activation. (P. Luppi and M. Trucco, *Immunological Models of Type 1 Diabetes,* 52 Horm. Res. 1 (1999)).

Systemic lupus erythematosus (SLE) is a non-organ specific autoimmune disease. The primary autoantigen responsible for the disease is not currently known. Although it was previously believed that DNA-AntiDNA complexes mediated the disease, it is now thought that nucleosomes and complement factor CLq play roles in the pathogenesis. (S. O. McLigeyo, *Pathogenesis of Lupus Nephritis: a Review*, 75 East Afr. Med. J, 628 (1998)).

Nephritis is a common complication of SLE. In this immune-mediated disease, nephritogenic autoantibodies which localize to the kidney are accompanied by activated macrophages and T cells as a result of enhanced, abnormal production of macrophage growth factors and cytokines. (M. H. Foster and V. R. Kelley, Lupus nephritis: Update on Pathogenesis and Disease Mechanisms, 19 Semin. Nephrol. 173 (1999)).

Rheumatoid arthritis is a chronic multisystem autoimmune inflammatory disease where an unknown autoantigen is presented to CD4+ T cells. The immune response primarily occurs in the synovial tissue and fluid of the joints. (Thomas R. MacDonald et al., *Dendritic Cells and the Pathogenesis of Rheumatoid Arthritis*, 66 J. Leukoc. Biol. 286 (1999)).

Although there are several treatments for the overt physiologically manifested symptoms of these disorders, an acute need exists for therapies which are directed toward the auto-immune mechanisms.

SUMMARY OF THE INVENTION

A primary aspect of the present invention is to provide a method for alleviating antibody-mediated auto-immune diseases by administering to a mammal an effective amount of a compound that inhibits the expression or induction of IL-16 expression and/or of RANTES expression. Some antibody-mediated inflammatory auto-immune disorders that can be treated by this method are Thyroid-Associated Ophthalmology (TAO), vitiligo, leukemia, rheumatoid arthritis, lymphoma, lupus, pemphigus, adrenal failure, polyglandular failure, and Type I diabetes. A preferred embodiment of the invention is the treatment of TAO in human patients by administering an effective amount of rapamycin, PD098059, or SB203580 or a combination thereof. Rapamycin and PD098059 disrupt the signaling pathway that leads IL-16 expression or induction and therefore to lymphocyte infiltration and hyaluronic acid accumulation in orbital tissues, thereby alleviating the inflammation that causes protopsis in patients with TAO.

Another aspect of the present invention is a diagnostic method to determine whether a patient has antibody-activated fibroblasts and is thus a candidate for treatment under the methods of the invention, by measuring serum levels of IL-16 and/or RANTES. A preferred embodiment of the invention employs enzyme-linked immunosorbent assay (ELISA) to measure the levels of IL-16 and RANTES in biological samples. The presence of antibody-activated fibroblasts may be used as a factor in diagnosing an antibody-mediated inflammatory auto-immune disorder in the patient or predicting the severity and duration of the active phase of the disease.

DESCRIPTION OF THE FIGURES

FIGS. 3A, 3B, and 3C show that the serum concentrations of IL-16 are elevated in patients with TAO (3A) and that IL-16 (3B) PGHS-2 protein (3C) can be detected in the orbital tissue of TAO patients.

FIG. 5 is an overview of the pathway of antibody-mediated auto-immune disorders alleviated or diagnosed by the present invention.

DETAILED DESCRIPTION OF THE INVENTION

Figure 1:
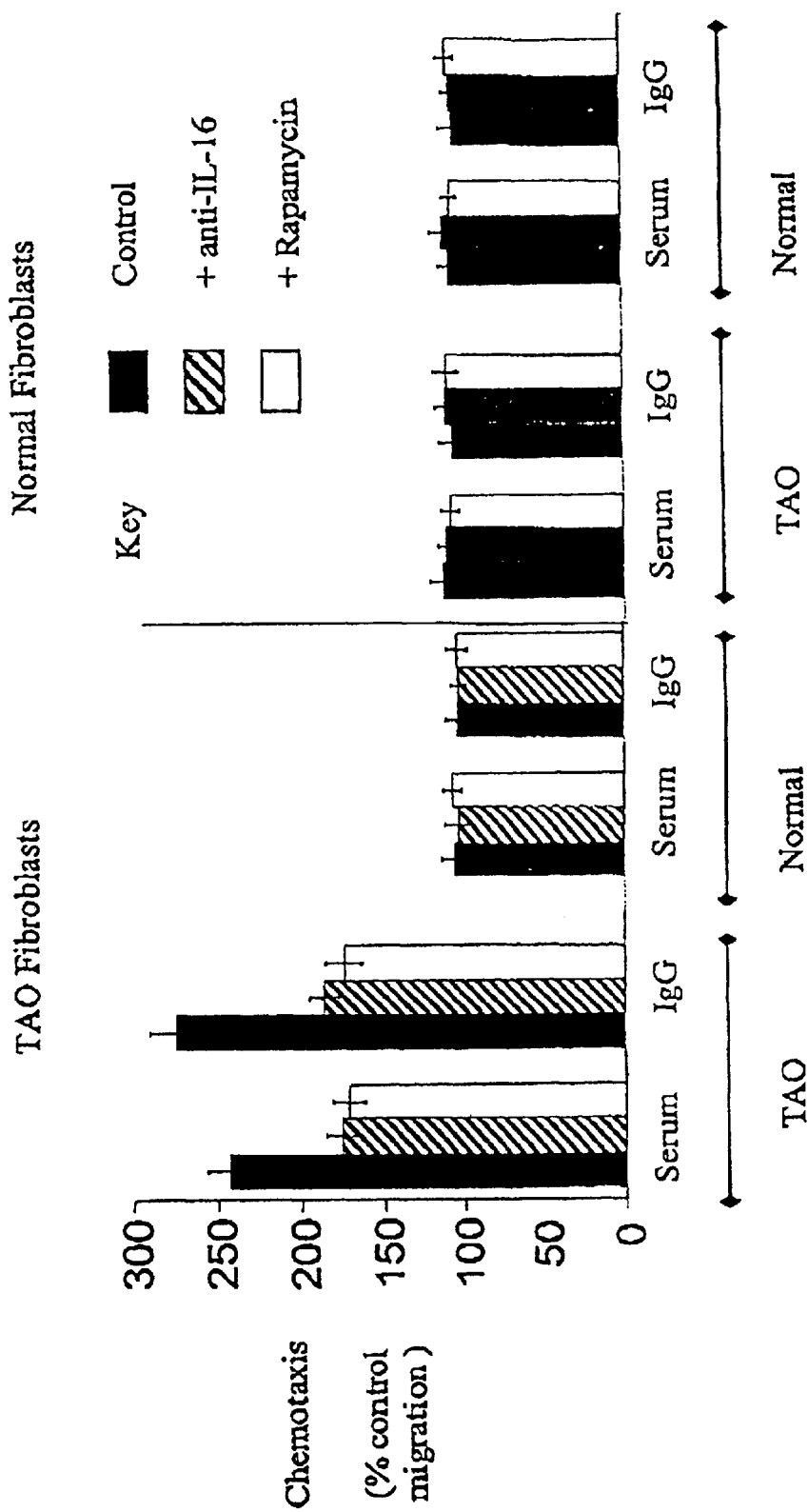
FIG. 1 shows that TAO fibroblasts exposed to either sera (1%) or to purified IgG (100 ng/ml) from donors with TAO exhibit a dramatic induction of IL-16 expression and release and that approximately 50% of the increase in chemoattractive activity is blocked by rapamycin.

As used herein, "antibody-mediated inflammatory auto-immune disorder" means any disease in which antibody binding to the cells of a tissue of the patient is thought to lead to infiltration and proliferation of the inflammatory cells of the patient's immune system into those tissues. A non-exclusive list of such disorders includes Graves' disease and associated ophthalmopathy (TAO), Type I diabetes, Rheumatoid Arthritis, Lymphoma, Lupus, Leukemia, Pemphigus, Vitiligo, Adrenal Failures, and Poly-glandular Failures.

As used herein, the term "effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "effective amount" will, obviously, vary with such factors as the particular condition being treated, the physical condition of the patient, the type of mammal being treated, the duration of the treatment, the nature of concurrent therapy (if any), and the specific formulations employed and the structure of the compounds or their derivatives.

As used herein, an "IL-16 activity inhibitor" is a compound that prevents the translation or transcription of the IL-16 gene, translation of IL-16 mRNA into protein, blocks the activation of pro-IL-16, or neutralizes the lymphocyte chemoattractive properties of IL-16 after it is released from the cell. Preferred translation inhibitors are rapamycin, PD098059, SB203580 (2'-Amino-3'-methoxyflavone; $C_{16}H_{13}NO_3$) Kültz, D., et al. 1998 J. Biol. Chem. 273, 13645, SB203580 Borsch-Haubold et al. J. Biol. Chem. 273, 28766 (1988) and wortmannin, which block the signaling pathways that culminate in the initiation of IL-16 translation. Caspase-3 cleaves bioactive IL-16 from the promolecule. Accordingly, caspase-3 inhibitors prevent the release of mature IL-16 and thereby inhibit IL-16 dependent lymphocytic chemotaxis. Anti-IL-16 antibodies bind bioactive IL-16 after its release from the cell, neutralizing the cell's IL-16-dependent lymphocyte chemoattractive ability.

As used herein, a "RANTES activity inhibitor" is a compound that prevents the translation or transcription of the RANTES gene, translation of a RANTES mRNA into protein, blocks the activation of RANTES, or neutralizes the lymphocyte chemoattractive properties of RANTES after it is released from the cell. The preferred inhibitor of RANTES which blocks the signaling pathways leading to the initiation of RANTES expression. SB203580 is a selective and cell-permeable compound that acts by inhibiting the activation of P38 MAP kinase and phosphorylation of P38 MAP kinase substrates. SB203580 is reported to block the increase of MAP kinase activity produced by nerve growth factor. The compound inhibits cell growth and reverses the phenotype of ras-transformed BALB 3T3 mouse fibroblasts and rat kidney cells. Anti-RANTES antibodies bind bioactive RANTES after its release from the cell, neutralizing the cell's RANTES-dependent lymphocyte chemoattractive ability.

As used herein "elevated level" means the level of analyte which is greater by a statistically significant amount than the level of analyte present in a particular biological sample of a mammal that is not suffering from an antibody-mediated inflammatory autoimmune disorder. For Graves' disease, an elevated level of IL-16 is times the level of IL-16 in a mammal that is not suffering from Graves' disease. This differentiation enables the diagnostic elements of the present invention as disclosed herein.

As used herein a "patient" is a mammal suspected of having an antibody-mediated inflammatory auto-immune disorder. The patient is preferably human but may also be another mammal.

As used herein a "biological sample" is a substance obtained from the patient's body. The particular "biological sample" selected will vary based on the disorder the patient is suspected of having and, accordingly, which biological sample is most likely to contain the analyte.

As used herein "antibody-activated fibroblasts" are fibroblasts to which antibodies of the patient's immune system have bound, thereby up-regulating the synthesis and ultimate release of chemoattractant molecules, such as IL-16 and/or RANTES.

The present invention is derived from the discovery of the role of the orbital fibroblast in the pathogenesis of TAO by virtue of its differential susceptibility to the up-regulation by inflammatory cytokines of hyaluronan and $PGE_2$ synthesis. These anatomic-site-specific activities of cytokines in fibroblasts explain the differentiation between orbital tissue, which manifests Graves' disease, and most other anatomic areas of connective tissue, which do not manifest Graves' disease. The role of cytokines from immunocompetent cells in the pathogenesis of TAO is established by the presence in the TAO orbit of lymphocytes and other bone marrow-derived cells known to produce and release these molecules. In addition, the aberrant expression of class II MHC HLA-DR in affected tissue implies that interferon-γ is present at a high concentration. Based on this evidence, the orbital fibroblasts are shown to be particularly susceptible to the actions of both IL-1 and leukoregulin.

IL-16, in concert with RANTES, a c-c chemokine, are the principal lymphocyte chemoattractants expressed and released by cytokine-activated human fibroblasts (Sciaky, D., Brazer, W., Center, D. M., Cruikshank, W. W. and Smith, T. J.: Cultured human fibroblasts express constitutive IL-16 mRNA: Cytokine induction of active IL-16 protein synthesis through a caspase-3-dependent mechanism. *J. Immunol.* 164(7):3806–14, 2000). Moreover, IL-16 and RANTES synthesis in TAO orbital fibroblasts, but not in fibroblasts from orbits or dermal sites of subjects without Graves disease, is an important target for TSI-dependent up-regulation, and thus may represent the critical pathway through which orbital disease is initiated. An important step in the discovery of the present invention was the elucidation of ways to halt the critical mechanisms through which TSI induces IL-16 and RANTES expression in TAO fibroblasts.

The regulation of protein translation involves a cascade of kinases that is inhibited by the immunosuppressive drug, rapamycin. It has been demonstrated recently that the translation of many, although not all mRNAs, is regulated by a pathway that culminates in a complex of three protein components that are termed, in aggregate, eukaryotic translation initiation factor-4E (eIF-4E). This complex interacts with the m7 cap of target mRNAs and recruits the 40S ribosomal subunit. The activity of eIF-4E is governed, in part, by a family of inhibitory polypeptides termed 4E-BPs. These 4E-BPs, when under-phosphorylated, bind and inhibit the activities of eIF-4E. But when they become phosphorylated at crucial amino acids their binding to eIF-4E is attenuated. Immediately up-stream from the 4E-BPs and proximately responsible for their phosphorylation is the FRAP/mTOR kinase. It is of significant importance to this proposal that the upstream pathway leading to 4E-BP phosphorylations is sensitive to the immunosuppressive drug, rapamycin. eIF-4E activity can also be regulated through gene transcription and by varying the relative levels of phosphorylation of eIF-4E itself. Cytokines and growth factors eliciting eIF-4E phosphorylations act, at least in part, through protein kinase C and MAP kinase that are insensitive to rapamycin. Another component of mRNA translational regulation which is sensitive to rapamycin and which targets a subset of mRNAs for translation, through an as yet undefined mechanism, is termed $p70^{s6k}$. Currently, nothing is known about any of these pathways that regulate mRNA translation in orbital fibroblasts. However, applicant has found that the rapamycin-sensitive pathway(s) are of critical importance to the activation of IL-16 mediated lymphocyte signaling by TSI in these fibroblasts.

TAO is characterized by a disordered accumulation of hyaluronan in inflammation in orbital soft tissues. Applicants have shown that fibroblasts derived from orbital endomysial and adipose/connective tissue are identical but differ dramatically from those emanating from outside the orbit (skin, subcutaneous, omental, breast and skeletal muscle). Orbital fibroblasts express a characteristic pattern of gangliosides and surface receptors. They are heterogeneous with regard to the surface display of Thy-1 and can be segregated into discrete populations on that basis. They have been characterized by us as expressing collagens I and III, fibronectin and vimentin but not markers of endothelial, epithelial or smooth muscle cells. Thus they engender many of the identifying features associated with fibroblasts. Moreover, applicants have demonstrated that they possess an ultrastructure identical to that of non-orbital fibroblasts (Henrikson, R. C. and Smith, T. J.: Ultrastructure of cultured human orbital fibroblasts. *Cell Tis. Res.* 278:629–6331, 1994).

Figure 2A:
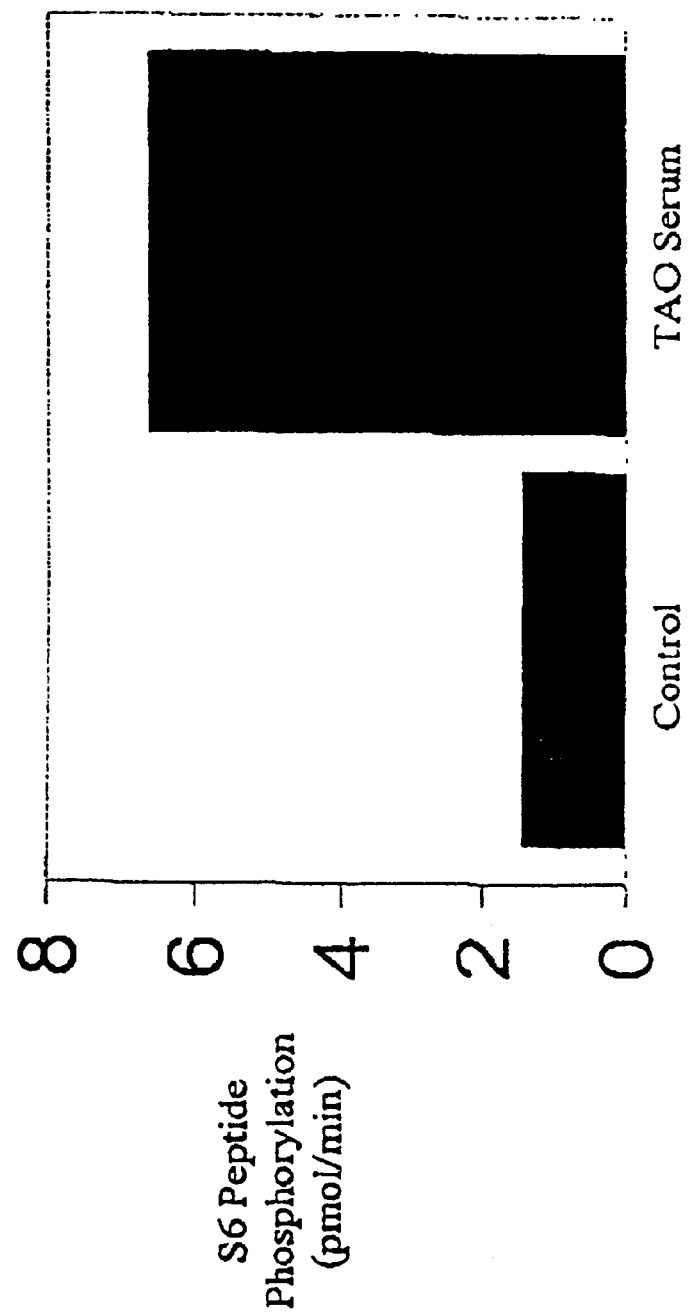
FIGS. 2A and 2B show activation of $p70^{s6K}$ by TSI 92A) and a schematic pathway of phosphorylation inhibition in a pathway that regulates, in part, translation of mRNA to protein.
Figure 2B:
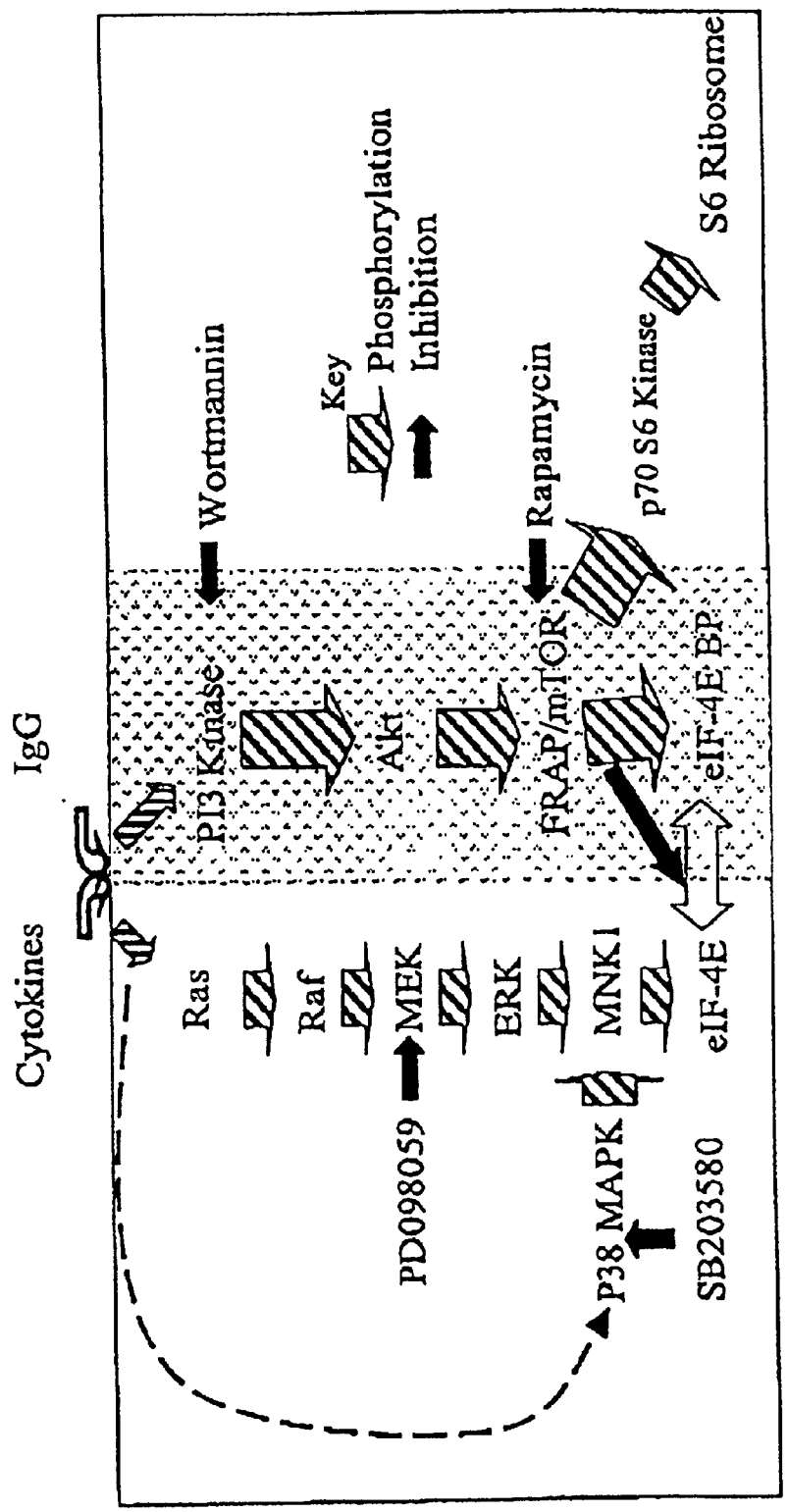

Applicants have also recently made a number of observations that appear directly relevant to the disordered accumulation of hyaluronan in TAO. Orbital fibroblasts synthesize less hyaluronan constitutively than do dermal fibroblasts (Smith, T. J., Bahn, R. S. and Gorman, C. A.: Hormonal regulation of hyaluronate synthesis in cultured human fibroblasts: evidence for differences between retroocular and dermal fibroblasts. *J. Clin. Endocrinol. Metab.* 69:1019–1023, 1989). However, Interferon-γ can modestly upregulate hyaluronan synthesis in orbital but not dermal fibroblasts (Smith, T. J., Bahn, R. S., Gorman, C. A. and Cheavens, M.: Stimulation of glycosaminoglycan accumulation by interferon gamma in cultured human retroocular fibroblasts. *J. Clin. Endocrinol. Metab.* 72:1169–1171, 1991). Upon investigation, applicant found that leukoregulin, a T cell-derived cytokine and IL-1β were found to dramatically up-regulate glycosaminoglycan synthesis in orbital fibroblasts (up to 15-fold above baseline) (FIG. 2A). The macromolecular material was sensitive to *Streptomyces* hyaluronidase digestion, defining it as hyaluronan (Smith, T. J., Wang, H. -S. and Evans, C. H.: Leukoregulin is a potent inducer of hyaluronan synthesis in cultured orbital fibroblasts. *Am. J. Physiol.* 268:C382–C388, 1995, appended). The increase was substantially greater in magnitude than that observed in dermal fibroblast strains from the same donors (3-fold) and on the basis of pulsechase studies could be attributed to changes in net synthesis. Thus, applicant has demonstrated an anatomic-site-preferential induction of hyaluronan synthesis in orbital fibroblasts.

Applicants have used cloned UDP-glucose dehydrogenase cDNAs to examine the expression and inducibility of this enzyme in orbital fibroblasts (Spicer, A. P., Kaback, L. A., Smith, T. J. and Seldin, M. F.: Molecular cloning, and characterization of the human and mouse UDP-glucose dehydrogenase genes. *J. Biol. Chem:* 273:25117–25124, 1998, appended). This mRNA is highly inducible in TAO orbital fibroblasts with IL-1β and leukoregulin. Our findings are unexpected since it had been assumed that this enzymatic step was not regulated. This, in our view, is a major advance because it potentially provides mechanistic insight into the normal and pathological regulation of the hyaluronan synthetic pathway. Applicants' observations suggest that multiple enzymes in the hyaluronan synthetic cascade in the orbit are regulated in orbital fibroblasts by extracellular cytokine messengers which are produced by infiltrating T-lymphocytes.

The pathogenesis of TAO, where T lymphocyte infiltration is a hallmark, involve the mechanisms of connective tissue lymphocyte signaling. Referring to FIG. 1, applicants have gathered evidence that IL-16, a CD4-specific ligand already associated with inflammation and autoimmunity, is a key participant in this disease process. All human fibroblasts thus far examined express high levels of IL-16 mRNA under basal culture conditions but no detectable IL-16 pro-molecule or mature protein are synthesized until the cells are activated with a pro-inflammatory cytokine such as IL-1β, leukoregulin and CD154. This pattern of IL-16 expression differs from that in other cell types, including CD8⁺ lymphocytes, mast cells and bronchial epithelium. The amount of IL-16 synthesized by fibroblasts is several-fold greater, on a per cell basis than that in these other cell types and it appears to be an important lymphocyte chemoattractant, in concert with RANTES, produced by fibroblasts. IL-1 activates the translation of the pre-formed IL-16 mRNA but steady-state levels of the transcript remain constant. IL-1β also activates caspase-3 in fibroblasts and inhibiting this enzyme precludes the cleavage of mature IL-16 protein from the pro-molecule or its release from the cell.

All human fibroblasts thus far examined, including many from anatomic regions not affected in Graves' disease, express the TSH-R and have begun to explore the functional consequences of this receptor expression on orbital fibroblasts (Bell, A., Grunder, L., Gagnon, A., Parikh, S. J., Smith, T. J. and Sorisky, A.: Expression of functional TSH receptor protein in human abdominal preadipocytes and orbital fibroblasts in primary culture. *Am. J. Physiol.* ((279: C335–340, 2000)). As discussed in Example 3, TAO fibroblasts exposed to either sera (1%) or to purified IgG (100 ng/ml) from donors with TAO exhibit a dramatic induction of IL-16 expression and release (See FIG. 1). Notably, fibroblasts from donors without known thyroid disease fail to exhibit this IL-16 response. Approximately 50–70% of the T lymphocyte chemoattractive activity released from IL-1 R-treated fibroblasts can be neutralized with an IL-16 blocking antibody. As demonstrated in Example 1, the remaining activity is susceptible to anti-RANTES antibodies, and, when neutralizing antibodies to both IL-16 and RANTES are added, virtually no chemoattractant activity remains.

As is further demonstrated in FIG. 1, approximately 50% of the increase in chemoattractive activity is blocked by rapamycin (20 nM), a specific inhibitor of the FRAP/mTOR pathway. When anti-IL-16 antibodies were added to rapamycin-treated fibroblast cultures, no further decrease in chemoattraction occurred, suggesting that rapamycin is blocking the IL-16-dependent lymphocyte migration activity. Levels of IL-16, assessed by ELISA, increase from being undetectable (in controls and TSI treated normal orbital cultures) to 538±51 pg/ml in the TSI-treated TAO cultures. This increase was blocked completely with rapamycin (20 nM).

As the data in FIG. 2A indicate, TSI activates $p70^{s6\kappa}$. Levels are consistently increased by at least 6-fold above controls after 1–3 hours of treatment. In contrast, IgG from individuals without Graves' disease fails to elicit either the IL-16 response or an activation of $P70^{s6k}$. Moreover, recombinant TSH does not activate the $p70^{s6k}$ pathway or induce IL-16 production. The effect of TSI on IL-16 synthesis is time-dependent and has been observed with sera and purified IgG from 6 different patients with severe TAO and has been replicated using three different TAO fibroblast strains. IL-16 synthesis-activating properties can be removed from TAO sera with protein A and can be eluted from protein A beads, suggesting that it is IgG that conveys both activities. This is a novel mechanism through which immunoglobulins might induce lymphocyte activation and migration.

Pursuant to this invention, IL-16 and RANTES are demonstrated to be relevant to the pathogenesis of TAO. Measurement of IL-16 in the sera of 7 individuals with severe, active TAO shows that the levels of this chemoattractant are consistently elevated compared to control sera from individuals without known thyroid disease (1102±356 pg1mI in TAO vs. 97±18 in controls; 11-fold elevation) (see FIG. 3A). Moreover, thin-sections of TAO orbital connective tissue exhibits specific immunostaining with an IL-16-specific polyclonal antibody (See FIG. 3B). Thus, IL-16 levels in orbital tissue and serum are increased considerably in TAO.

Based on the current results, Graves' disease-specific IgG, invariably found in individuals with TAO, interacts with orbital fibroblasts to induce IL-16 protein expression. This results in lymphocyte trafficking to the orbit. This invention yields a molecular rationale for why lymphocytes infiltrate the orbit in TAO, which we believe to be an important step in stimulating the cytokine-induced hyaluronic acid synthesis pathway.

Figure 4:
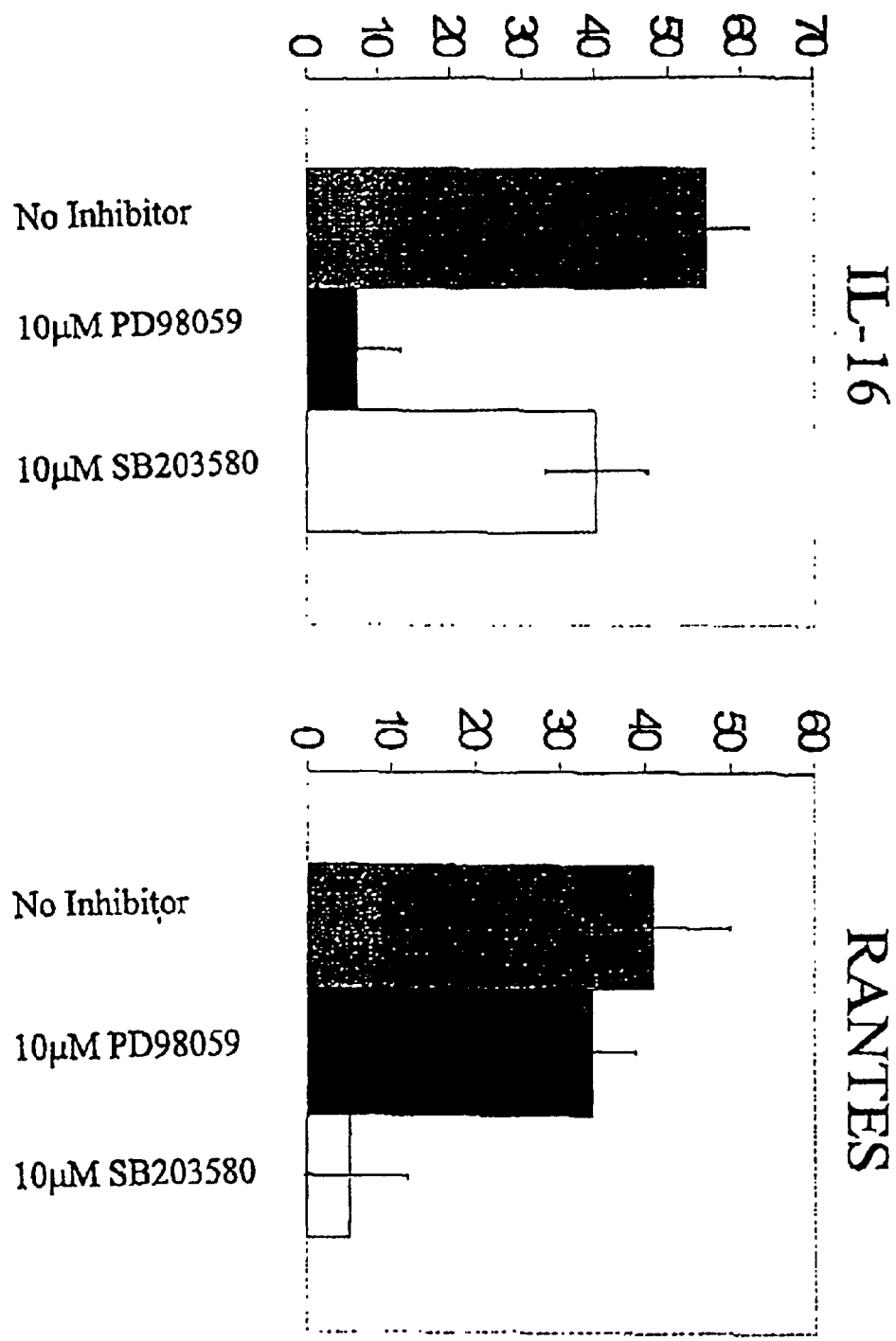
FIG. 4 shows the action of SB203580 and PD098059 on IL-16 and RANTES.

Referring to FIG. 5, these findings on the role of IL-16 and RANTES in the fibroblast/lymphocyte inflammation cascade provide options for therapies for TAO and other antibody-mediated inflammatory auto-immune disorders. The method of the therapeutic aspect of the invention involves inhibiting the activity of the two chemoattractant molecules that the applicants have shown lead to the majority of the inflammation cascade, IL-16 and RANTES. IL-16 activity inhibitors include, but are not limited to, rapapmycin, wortmannin, caspase-3 inhibitor, and anti-IL-16 antibody. RANTES activity inhibitors include, but are not limited to, SB203580, and anti-RANTES antibody. Referring to FIG. 4, the data demonstrate the action of SB203580 and PD098059 on IL-16 and RANTES. These compounds either block translation of the chemoattractant molecules, prevent release of chemoattractant molecules from the cell after they are translated, or neutralize the chemoattractant molecules' ability to cause lymphocytic chemotaxis after they are released.

Rapamycin, wortmannin and PD098059 are inhibitors which block the signaling pathway that culminates in the initiation of IL-16 translation. Recent studies indicate that rapamycin and wortmannin accomplish this by inhibiting the phosporylation of a key protein in a pathway that regulates, among other things, the translation of mRNA to protein. In their unphosphorylated form, these 4E-BPs bind and inhibit translation initiation factor-4E, which is responsible for recruitment of the 40S ribosomal subunit. Rapamycin also acts on $p70^{S6k}$, another component of mRNA translational regulation, which targets a subset of mRNA for translation through an as yet undefined mechanism.

Caspase-3 inhibitor prevents the cleavage of bioactive IL-16 from its promolecule, thereby blocking release from the cell. The protein sequence of the caspase-3 inhibitor is (Ac-Asp-Glu-Val-Asp-aldehyde)[3], as described in Sciaky, D. et al., J. Immunol. 164(7):3806–14, 2000.

Anti-IL-16 and anti-RANTES antibodies neutralize the chemoattractant characteristics of IL-16 and RANTES, respectively, after they are released from the cell. In a preferred embodiment of the invention in which the antibodies are administered to a human, humanized anti-IL-16 and humanized anti-RANTES are prepared in a manner similar to the method described in U.S. Pat. No. 6,054,297.

Any suitable dosage of the compounds may be given in the method of the invention. Dosage levels and requirements are well-recognized by those of ordinary skill in the art. As one of ordinary skill in the art will appreciate, lower or higher doses may be required depending on particular factors. For instance, specific dosage and treatment regimens will depend on facts such as the mammal's general health profile, the type of antibody-mediated auto-immune disorder being treated, the severity and course of the patient's disorder, and the judgment of the treating physician.

Dosage forms of the compounds of this invention include pharmaceutically acceptable carriers known to those of ordinary skill in the art. Pharmaceutically acceptable components are those that are suitable for use with mammals without undue adverse side effects (such as toxicity, irritation, and allergic response) commensurate with a reasonable benefit/risk ratio. The carrier can be a solid or liquid and the type is generally chosen based on the type of administration being used. The active agent can be coadministered in the form of a tablet or capsule, as an agglomerated powder or in a liquid form. Examples of suitable solid carriers include lactose, sucrose, gelatin and agar. Capsule or tablets can be easily formulated and can be made easy to swallow or chew; other solid forms include granules and bulk powders. Tablets may contain suitable binders, lubricants, diluents, disintegrating agents, coloring agents, flavoring agents, flow-inducing agents and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners and melting agents. Parenteral and intravenous forms may also include isotonic salts and other materials to make them compatible with the type of injection or delivery system chosen.

The method of administration can be any suitable method which effectively alleviates the particular antibody-mediated inflammatory auto-immune disorder being treated. Possible ways in which the treatment may be administered are orally, rectally, parenterally, enterically, subcutaneously, transdermally, peritoneally, or intravenously.

In addition to its therapeutic aspects, the present invention also relates to a diagnostic method for detecting the presence of antibody-activated fibroblasts in the patient. Applicants believe that several auto-immune diseases or disorders are associated with antibody-activated fibroblasts. Applicants have shown that increased activation of fibroblasts by auto-antibodies can be monitored by determining the levels of IL-16 and/or RANTES production in a patient. Altered levels of these chemoattractants can be detected in various biological samples in mammals, preferably humans. Levels of IL-16 and/or RANTES may be monitored in a patient, using standard techniques, as an indication of the deleterious aspects of the disease condition. Biological samples, including but not limited to serum, vitreous humor, aqueous humor, synovial fluid, and tissue, will be drawn from the patient using standard techniques. Particularly preferred are serum samples. The measurement of the IL-16 and RANTES levels may be monitored using any method possible to detect the levels of these proteins in biological samples. A preferred method of analysis is by ELISA as described in Sciaky, D. et al., J. Immunol. 164(7):3806–14, 2000. An ELISA specific for IL-16 can be used to assess the levels released by fibroblasts as described previously in Lim, K. G. et al., J. Immunol. 156(7): 2566–70, 1996. An ELISA specific for RANTES can be used according to the manufacturer's specification (BioSource Intl., Camarillo, Calif.).

The following examples serve merely to illustrate the invention, and should not be construed as limiting the invention to any particular embodiment.

EXAMPLE 1

Production of IL-16 and RANTES by Orbital Fibroblasts Upon Stimulation by TSI and Resultant Chemoattractant Activity Orbital tissue in TAO becomes inflamed and infiltrated with lymphocytes and mast cells. Although the reason why immunologically competent cells are trafficked to the orbit is uncertain, applicants have presented preliminary evidence that the production of the CD4-specific chemoattractant, IL-16, is dramatically induced by TSI in TAO but not in normal orbital fibroblasts, (see FIG. 1). This experiment demonstrates that the expression of chemoattractants in the TAO orbit is the basis for T lymphocyte recruitment, and that the 50% of chemoattractive activity not accounted for by IL-16 is RANTES. This experiment demonstrates the role of IL-16 and RANTES in the lymphocyte migration activity emanating from orbital fibroblasts by neutralization of these proteins with specific antibodies.

The general migration assay is described in detail in Sciaky, D., et al., "Cultured human fibroblasts express constitutive IL-16 mRNA: Cytokine induction of active IL-16 protein synthesis through a caspase-3-dependent mechanism," J. Immunol. 164(7):3806–14 (2000), hereby incorporated fully by reference. Briefly, fibroblasts from TAO and normal orbital tissue were seeded in 24-well arrays and grown to confluence. Monolayers were shifted containing 1% FBS to which nothing, purified normal or TAO IgG was added for various time intervals. Medium was collected and stored until use at −80° C. Chemotaxis was examined using Boyden chambers to which NWNA-T lymphocytes were added as the cellular targets. 50 μl cell suspension ($10^7$ cells/ml) were placed in the upper compartments of 48-well micro-chemotaxis chambers separated from 32 μl of serum samples by 8 μm micropore nitrocellulose filters (Neuroprobe). These were incubated at 37° C. in 5% $CO_2$ environment for 3 hr. Filters were fixed, stained with hematoxylin, dehydrated, mounted on glass slides and viewed by light microscopy. Lymphocyte migration was quantified by counting the total number of cells migrating beyond a fixed depth. This depth was set to routinely identify a baseline migration under control conditions of 10–15 cells per high power field. Five such fields were counted in duplicate for each sample and the means±SD were calculated and expressed as percentage values of baseline cell migration in control buffer alone (100%). For each set of experimental conditions, at least three separate determinations were performed. Differences between experimental groups were analyzed by the Student t test using absolute values obtained for lymphocyte migration and statistical difference was accepted at the 95% level of confidence.

To assess specificity for IL-16, experiments were conducted by incubating samples of culture media for 15 min with neutralizing concentrations of anti-IL-16 MAB (clone 14. 1, 10 μg/ml), which blocks the chemotactic activity of 50 ng/ml of rIL-16. Anti-RANTES MAB (5 μg/ml) having an $ND_{50}$ of 200 ng/ml rRANTES was used to neutralize RANTES as described in Sciaky D., Brazer, W., Center, D. M., Cruikshank, W. W. and Smith, T. J.: Cultured human fibroblasts express constitutive IL-16 mRNA: Cytokine induction of active IL-16 protein synthesis through a caspase-3-dependent mechanism. *J. Immunol.* 164(7):3806–14, 2000).

The levels of IL-16 and RANTES were then assessed with specific ELISAs. The ELISA assay for IL-16 is performed essentially as discussed in Sciaky D., Brazer, W., Center, D. M., Cruikshank, W. W. and Smith, T. J.: Cultured human fibroblasts express constitutive IL-16 mRNA: Cytokine induction of active IL-16 protein synthesis through a caspase-3-dependent mechanism. *J. Immunol.* 164(7):3806–14, 2000). An ELISA (BioSource) for RANTES was performed according to the manufacturer's instructions. In an analysis of over a dozen strains, TAO specific IgG elicit substantial induction of IL-16 and RANTES and in no case were normal fibroblasts so affected.

Whether TSIs up-regulate IL-16 at a pre-translational level was assessed by performing northern blot analysis using a probe generated from a full-length cDNA as described in the Sciaky D., Brazer, W., Center, D. M., Cruikshank, W. W. and Smith, T. J.: Cultured human fibroblasts express constitutive IL-16 mRNA: Cytokine induction of active IL-16 protein synthesis through a caspase-3-dependent mechanism. *J. Immunol.* 164(7):3806–14, 2000). A similar northern blot analysis was performed using a full length cDNA probe for RANTES.

As demonstrated by the data, IL-16 and RANTES are the dominant components of T lymphocyte chemoattraction generated by TSI-activated TAO fibroblasts.

EXAMPLE 2

Demonstration of Identity between TSI and the IgG TAO Serum Factor Which Activates TAO Ocular Fibroblasts As described above, applicants have found that a component of TAO serum, binding to protein A, activates the synthesis and release of mature IL-16 and other chemoattractive activity from TAO orbital fibroblasts. This activity is manifested only in TAO but not normal orbital fibroblasts. This experiment demonstrates that the fibroblast-activating IgG belongs to the same subclass as classic TSI, which is an IgG1, and presents other evidence in support of the proposition that the component of TAO serum which activates TAO fibroblasts is, in fact, TSI.

First, sera was incubated with beads containing anti-heavy chain-specific antibodies, which verified that the immunoglobulin is IgG and not IgM. The adsorbed IgG was eluted either with high salt concentrations or low pH. Aliquots of the material were then passed over a series of IgG isotype-specific columns commercially available from Pharmingen, R & D and Sigma. The purity of the materials adsorbed to these affinity matrices was verified by subjecting them to isotype-specific ELISAs (Sigma).

At each step of the purification process, an aliquot was assayed for IL-16-inducing activity in TAO fibroblasts to verify the presence of activity. The aliquot was also assayed for activity in the primary thyrocyte culture system described in Gianoukakis, A. G., et al., "Prostaglandin endoperoxide H synthase expression in cultured thyroid epithelial cells: Potential contributions to glandular inflammation" to determine whether cAMP generation and thyroid hormone synthesis (classical TSI activities) are up-regulated.

The data demonstrate that the active serum component is an IgG, as verified in 5 additional sera samples from patients with TAO. As can be seen from the control sera from normal control donors without known thyroid disease, the immunoglobulin constituent of the TAO serum responsible for fibroblast activation is specific to Graves' disease.

EXAMPLE 3

Demonstration of the Inhibition of IL-16 Activity in Fibroblasts by Rapamycin

Confluent fibroblasts harvested from patients with Graves' disease or from patients without known thyroid disease are grown to confluence and then are incubated in the presence or absence of either whole serum (1%) or approximately 100 ng IgG purified from that serum for 24 hours. The source of the serum and IgG was either from patients with Graves' disease or control (normal) subjects. Following incubation, the medium is collected, frozen, and then used in a lymphocyte migration assay as described in Sciaky et al (Journal of Immunology 164(7):3806–3814, 2000.

EXAMPLE 4

Increased Levels of IL-16 and RANTES in Serum and Tissues of TAO Patients

Referring to FIGS. 3A–3C, the concentration of IL-16 is determined in sera from either patients with Graves' disease or normal controls. The sera are subjected to an ELISA assay, which utilizes an anti-IL-16 specific antibody. (Courtesy Dr. Cruikshank; Boston University.) IL-16 was detected by standard immunohistochemical techniques in thin sections harvested from affected orbital connective tissues from a patient with severe Graves' ophthalmopathy.

All publications mentioned in this specification are herein incorporated by reference to the same extent as if each individual publication was specifically and individually indicated to be incorporated by reference.

We claim:

1. A method of detecting thyroid-associated ophthalmopathy in a patient comprising:

obtaining a biological sample from the patient, isolating IgG from the patient sample, exposing the IgG to orbital fibroblasts from patients with thyroid-associated ophthalmopathy, measuring the level of
IL-16 or
RANTES produced by the orbital fibroblasts,
wherein an elevated level of IL-16 or RANTES, as compared to normal control indicates the presence or severity of thyroid-associated ophthalmopathy in the patient.

2. The method of claim 1 wherein the level of IL-16 or RANTES is measured by an Enzyme-Linked Immunosorbent Assay (ELISA).

3. The method of claim 1 wherein the patient is human.

4. The method of claim 1 wherein the biological sample is selected from the group consisting of:
blood,
synovial fluid,
ascites, and
tissue.

* * * * *

UNITED STATES PATENT AND TRADEMARK OFFICE
CERTIFICATE OF CORRECTION

PATENT NO.    : 6,936,426 B2
DATED         : August 30, 2005
INVENTOR(S)   : Smith, Terry J. et al.

It is certified that error appears in the above-identified patent and that said Letters Patent is hereby corrected as shown below:

Column 15,
Line 5, delete "normal control indicates" and replace with -- normal controls, indicates --.

Signed and Sealed this

Twenty-third Day of May, 2006

JON W. DUDAS
*Director of the United States Patent and Trademark Office*